United States Patent
Reinke et al.

(10) Patent No.: US 8,504,165 B2
(45) Date of Patent: *Aug. 6, 2013

(54) CLOCK SYNCHRONIZATION IN AN IMPLANTABLE MEDICAL DEVICE SYSTEM

(71) Applicant: Medtronic, Inc., Minneapolis, MN (US)

(72) Inventors: James D. Reinke, Maple Grove, MN (US); Robert M. Ecker, Lino Lakes, MN (US); Kaustubh R. Patil, Blaine, MN (US); Michael B. Terry, Camas, WA (US); Jonathan P. Roberts, Coon Rapids, MN (US); Robert A. Corey, Arden Hills, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/746,818

(22) Filed: Jan. 22, 2013

(65) Prior Publication Data

US 2013/0138991 A1    May 30, 2013

Related U.S. Application Data

(62) Division of application No. 12/697,070, filed on Jan. 29, 2010, now Pat. No. 8,396,563.

(51) Int. Cl.
*A61N 1/36* (2006.01)
*A61N 1/378* (2006.01)

(52) U.S. Cl.
USPC .................................. 607/60; 607/2; 607/32

(58) Field of Classification Search
USPC ......................................... 607/30–32, 59, 60
See application file for complete search history.

(56) References Cited

U.S. PATENT DOCUMENTS

| | | | |
|---|---|---|---|
| 3,651,454 A | 3/1972 | Venema et al. |
| 3,682,160 A | 8/1972 | Murata |
| 3,717,858 A | 2/1973 | Hadden |
| 3,735,396 A | 5/1973 | Getchell |
| 3,742,473 A | 6/1973 | Hadden |
| 3,805,795 A | 4/1974 | Denniston et al. |
| 3,857,399 A | 12/1974 | Zacouto |
| 3,891,914 A | 6/1975 | Akita |
| 3,922,490 A | 11/1975 | Pettis |
| 3,938,144 A | 2/1976 | Pederson et al. |

(Continued)

FOREIGN PATENT DOCUMENTS

| | | |
|---|---|---|
| EP | 0 235 482 A1 | 9/1987 |
| EP | 0 356 603 B1 | 11/1993 |

(Continued)

OTHER PUBLICATIONS

Invitation to Pay Additional Fees for PCT/US2010/033408, dated Aug. 16, 2010. (4 pp.).

(Continued)

*Primary Examiner* — Allen Porter, Jr.
(74) *Attorney, Agent, or Firm* — Evans M. Mburu

(57) ABSTRACT

This disclosure is directed to the synchronization of clocks of a secondary implantable medical device (IMD) to a clock of a primary IMD. The secondary IMD includes a communications clock. The communications clock may be synchronized based on at least one received communications pulse. The secondary IMD further includes a general purpose clock different than the communications clock. The general purpose clock may be synchronized based on at least one received power pulse. The communications clock may also be synchronized based on the at least one received power pulse.

18 Claims, 9 Drawing Sheets

U.S. PATENT DOCUMENTS

| | | |
|---|---|---|
| 3,958,558 A | 5/1976 | Dunphy et al. |
| 3,959,772 A | 5/1976 | Wakasa et al. |
| 4,016,480 A | 4/1977 | Hofmann |
| 4,023,562 A | 5/1977 | Hynecek et al. |
| 4,063,220 A | 12/1977 | Metcalfe et al. |
| 4,077,030 A | 2/1978 | Helava |
| 4,093,946 A | 6/1978 | Fowler |
| 4,101,337 A | 7/1978 | Dano |
| 4,114,606 A | 9/1978 | Seylar |
| 4,127,845 A | 11/1978 | Dansbach et al. |
| 4,137,910 A | 2/1979 | Murphy |
| 4,139,737 A | 2/1979 | Shimada et al. |
| 4,202,339 A | 5/1980 | Wirtzfeld et al. |
| 4,211,238 A | 7/1980 | Shu et al. |
| 4,227,181 A | 10/1980 | Brittain |
| 4,265,252 A | 5/1981 | Chubbuck et al. |
| 4,266,554 A | 5/1981 | Hamaguri |
| 4,272,758 A | 6/1981 | Giraud |
| 4,293,947 A | 10/1981 | Brittain |
| 4,311,986 A | 1/1982 | Yee |
| 4,360,030 A | 11/1982 | Citron et al. |
| 4,364,397 A | 12/1982 | Citron et al. |
| 4,399,820 A | 8/1983 | Wirtzfeld et al. |
| 4,407,296 A | 10/1983 | Anderson |
| 4,413,250 A | 11/1983 | Porter et al. |
| 4,417,306 A | 11/1983 | Citron et al. |
| 4,420,753 A | 12/1983 | Meyer-Ebrecht |
| 4,422,066 A | 12/1983 | Belcourt et al. |
| 4,432,372 A | 2/1984 | Monroe |
| 4,467,807 A | 8/1984 | Bornzin |
| 4,485,813 A | 12/1984 | Anderson et al. |
| 4,494,950 A | 1/1985 | Fischell |
| 4,519,401 A | 5/1985 | Ko et al. |
| 4,534,025 A | 8/1985 | Floyd |
| 4,535,401 A | 8/1985 | Penn |
| 4,538,262 A | 8/1985 | Sinniger et al. |
| 4,539,992 A | 9/1985 | Calfee et al. |
| 4,543,955 A | 10/1985 | Schroeppel |
| 4,566,456 A | 1/1986 | Koning et al. |
| 4,592,364 A | 6/1986 | Pinto |
| 4,600,017 A | 7/1986 | Schroeppel |
| 4,628,934 A | 12/1986 | Pohndorf et al. |
| 4,671,288 A | 6/1987 | Gough |
| 4,708,143 A | 11/1987 | Schroeppel |
| 4,712,555 A | 12/1987 | Thornander et al. |
| 4,716,887 A | 1/1988 | Koning et al. |
| 4,730,619 A | 3/1988 | Koning et al. |
| 4,738,267 A | 4/1988 | Lazorthes et al. |
| 4,745,596 A | 5/1988 | Sato |
| 4,750,495 A | 6/1988 | Moore et al. |
| 4,779,199 A | 10/1988 | Yoneda et al. |
| 4,791,935 A | 12/1988 | Baudino et al. |
| 4,794,372 A | 12/1988 | Kazahaya |
| 4,802,481 A | 2/1989 | Schroeppel |
| 4,807,629 A | 2/1989 | Baudino et al. |
| 4,808,994 A | 2/1989 | Riley |
| 4,813,421 A | 3/1989 | Baudino et al. |
| 4,815,469 A | 3/1989 | Cohen et al. |
| 4,821,735 A | 4/1989 | Goor et al. |
| 4,827,933 A | 5/1989 | Koning et al. |
| 4,841,981 A | 6/1989 | Tanabe et al. |
| 4,846,191 A | 7/1989 | Brockway et al. |
| 4,858,615 A | 8/1989 | Meinema |
| 4,860,751 A | 8/1989 | Callaghan |
| 4,867,161 A | 9/1989 | Schaldach |
| 4,867,163 A | 9/1989 | Schaldach |
| 4,873,980 A | 10/1989 | Schaldach |
| 4,877,032 A | 10/1989 | Heinze et al. |
| 4,881,410 A | 11/1989 | Wise et al. |
| 4,886,064 A | 12/1989 | Strandberg |
| 4,899,760 A | 2/1990 | Jaeb et al. |
| 4,903,701 A | 2/1990 | Moore et al. |
| 4,926,875 A | 5/1990 | Rabinovitz et al. |
| 4,936,304 A | 6/1990 | Kresh et al. |
| 4,941,472 A | 7/1990 | Moden et al. |
| 4,941,473 A | 7/1990 | Tenerz et al. |
| 4,947,854 A | 8/1990 | Rabinovitz et al. |
| 4,967,748 A | 11/1990 | Cohen |
| 4,967,755 A | 11/1990 | Pohndorf |
| 4,984,572 A | 1/1991 | Cohen |
| 4,986,270 A | 1/1991 | Cohen |
| 5,003,976 A | 4/1991 | Alt |
| 5,016,631 A | 5/1991 | Hogrefe |
| 5,016,641 A | 5/1991 | Schwartz |
| 5,021,777 A | 6/1991 | Gross et al. |
| 5,025,786 A | 6/1991 | Siegel |
| 5,040,536 A | 8/1991 | Riff |
| 5,040,538 A | 8/1991 | Mortazavi |
| 5,058,586 A | 10/1991 | Heinze |
| 5,065,759 A | 11/1991 | Begemann et al. |
| 5,076,271 A | 12/1991 | Lekholm et al. |
| 5,085,213 A | 2/1992 | Cohen |
| 5,087,243 A | 2/1992 | Avitall |
| 5,097,831 A | 3/1992 | Lekholm |
| 5,109,850 A | 5/1992 | Blanco et al. |
| 5,113,859 A | 5/1992 | Funke |
| 5,113,868 A | 5/1992 | Wise et al. |
| 5,129,394 A | 7/1992 | Mehra |
| 5,156,157 A | 10/1992 | Valenta, Jr. et al. |
| 5,166,678 A | 11/1992 | Warrior |
| 5,174,303 A | 12/1992 | Schroeppel |
| 5,184,614 A | 2/1993 | Collins et al. |
| 5,186,169 A | 2/1993 | Schaldach |
| 5,205,286 A | 4/1993 | Soukup et al. |
| 5,207,103 A | 5/1993 | Wise et al. |
| 5,228,176 A | 7/1993 | Bui et al. |
| 5,243,976 A | 9/1993 | Ferek-Petric et al. |
| 5,256,912 A | 10/1993 | Rios |
| 5,261,401 A | 11/1993 | Baker et al. |
| 5,265,615 A | 11/1993 | Frank et al. |
| 5,267,564 A | 12/1993 | Barcel et al. |
| 5,275,171 A | 1/1994 | Barcel |
| 5,282,839 A | 2/1994 | Roline et al. |
| 5,293,879 A | 3/1994 | Vonk et al. |
| 5,304,208 A | 4/1994 | Inguaggiato et al. |
| 5,316,001 A | 5/1994 | Ferek-Petric et al. |
| 5,324,316 A | 6/1994 | Schulman et al. |
| 5,324,326 A | 6/1994 | Lubin |
| 5,325,870 A | 7/1994 | Kroll et al. |
| 5,330,505 A | 7/1994 | Cohen |
| 5,336,243 A | 8/1994 | Schaldach |
| 5,336,253 A | 8/1994 | Gordon et al. |
| 5,342,404 A | 8/1994 | Alt et al. |
| 5,353,800 A | 10/1994 | Pohndorf et al. |
| 5,358,514 A | 10/1994 | Schulman et al. |
| 5,365,930 A | 11/1994 | Takashima et al. |
| 5,368,040 A | 11/1994 | Carney |
| 5,391,190 A | 2/1995 | Pederson et al. |
| 5,394,400 A | 2/1995 | Phoy |
| 5,409,009 A | 4/1995 | Olson |
| 5,411,532 A | 5/1995 | Mortazavi |
| 5,417,717 A | 5/1995 | Salo et al. |
| 5,423,869 A | 6/1995 | Poore et al. |
| 5,431,172 A | 7/1995 | Hoegnelid et al. |
| 5,438,987 A | 8/1995 | Thacker et al. |
| 5,451,940 A | 9/1995 | Schneider et al. |
| 5,454,838 A | 10/1995 | Vallana et al. |
| 5,464,435 A | 11/1995 | Neumann |
| 5,470,348 A | 11/1995 | Neubauer et al. |
| 5,474,754 A | 12/1995 | Saxton et al. |
| 5,488,307 A | 1/1996 | Plott |
| 5,490,323 A | 2/1996 | Thacker et al. |
| 5,496,361 A | 3/1996 | Moberg et al. |
| 5,497,772 A | 3/1996 | Schulman et al. |
| 5,499,627 A | 3/1996 | Steuer et al. |
| 5,507,737 A | 4/1996 | Palmskog |
| 5,518,001 A | 5/1996 | Snell |
| 5,535,752 A | 7/1996 | Halperin et al. |
| 5,549,652 A | 8/1996 | McClure et al. |
| 5,564,434 A | 10/1996 | Halperin et al. |
| 5,593,430 A | 1/1997 | Renger |
| 5,617,235 A | 4/1997 | Abrahamson |
| 5,628,777 A | 5/1997 | Moberg et al. |
| 5,684,451 A | 11/1997 | Seberger et al. |
| 5,693,075 A | 12/1997 | Plicchi et al. |
| 5,697,958 A | 12/1997 | Paul et al. |
| 5,700,283 A | 12/1997 | Salo |

| | | |
|---|---|---|
| 5,701,895 A | 12/1997 | Prutchi et al. |
| 5,702,427 A | 12/1997 | Ecker et al. |
| 5,715,827 A | 2/1998 | Corl et al. |
| 5,722,996 A | 3/1998 | Bonnet et al. |
| 5,722,998 A | 3/1998 | Prutchi et al. |
| 5,725,562 A | 3/1998 | Sheldon |
| 5,735,883 A | 4/1998 | Paul et al. |
| 5,740,596 A | 4/1998 | Corl et al. |
| 5,741,211 A | 4/1998 | Renirie et al. |
| 5,751,154 A | 5/1998 | Tsugai |
| 5,773,270 A | 6/1998 | D'Orazio et al. |
| 5,782,883 A | 7/1998 | Kroll et al. |
| 5,785,657 A | 7/1998 | Breyer et al. |
| 5,791,344 A | 8/1998 | Schulman et al. |
| 5,792,195 A | 8/1998 | Carlson et al. |
| 5,797,395 A | 8/1998 | Martin |
| 5,810,735 A | 9/1998 | Halperin et al. |
| 5,812,802 A | 9/1998 | Bahout et al. |
| 5,836,987 A | 11/1998 | Baumann et al. |
| 5,843,135 A | 12/1998 | Weijand et al. |
| 5,885,471 A | 3/1999 | Ruben et al. |
| 5,899,927 A | 5/1999 | Ecker et al. |
| 5,902,326 A | 5/1999 | Lessar et al. |
| 5,905,766 A | 5/1999 | Nguyen |
| 5,911,738 A | 6/1999 | Sikorski et al. |
| 5,917,346 A | 6/1999 | Gord |
| 5,918,110 A | 6/1999 | Abraham-Fuchs et al. |
| 5,928,344 A | 7/1999 | Stierli |
| 5,935,081 A | 8/1999 | Kadhiresan |
| 5,936,520 A | 8/1999 | Luitje et al. |
| 5,954,752 A | 9/1999 | Mongeon et al. |
| 5,957,957 A | 9/1999 | Sheldon |
| 5,977,431 A | 11/1999 | Knapp et al. |
| 5,977,803 A | 11/1999 | Tsugai |
| 5,985,129 A | 11/1999 | Gough et al. |
| 5,986,497 A | 11/1999 | Tsugai |
| 5,995,860 A | 11/1999 | Sun et al. |
| 5,999,848 A | 12/1999 | Gord et al. |
| 6,002,963 A | 12/1999 | Mouchawar et al. |
| 6,017,313 A | 1/2000 | Bratteli et al. |
| 6,024,704 A | 2/2000 | Meador et al. |
| 6,025,670 A | 2/2000 | Corl et al. |
| 6,038,475 A | 3/2000 | Sikorski et al. |
| 6,038,480 A | 3/2000 | Hrdlicka et al. |
| 6,070,103 A | 5/2000 | Ogden |
| 6,988,215 B2 | 1/2006 | Splett et al. |
| 7,013,178 B2 | 3/2006 | Reinke et al. |
| 7,139,613 B2 | 11/2006 | Reinke et al. |
| 7,180,332 B2 | 2/2007 | Di Gregorio |
| 7,493,174 B2 | 2/2009 | Belalcazar et al. |
| 2002/0040234 A1 | 4/2002 | Linberg |
| 2003/0014082 A1 | 1/2003 | Schu et al. |
| 2003/0114898 A1 | 6/2003 | Von Arx et al. |
| 2004/0059396 A1 | 3/2004 | Reinke et al. |
| 2004/0122490 A1 | 6/2004 | Reinke et al. |
| 2007/0293915 A1 | 12/2007 | Kilgore et al. |
| 2009/0062880 A1 | 3/2009 | Li et al. |
| 2009/0118808 A1 | 5/2009 | Belacazar et al. |

FOREIGN PATENT DOCUMENTS

| | | |
|---|---|---|
| EP | 1 040 848 A1 | 8/2003 |
| WO | 88/00446 | 1/1988 |
| WO | 89/01315 | 5/1989 |
| WO | 2005061044 A1 | 7/2005 |

OTHER PUBLICATIONS

Franklin et al., "Proposed Standard IEEE P1073 Medical Information Bus Medical Device to Host Computer Interface Network Overview and Architecture," pp. 574-578, 1989.
International Search Report and Written Opinion from PCT/US2010/033408, dated Dec. 2, 2010, (18 pp).
Reinke, "Declaration Under 37 C.F.R. 1.132," Jan. 6, 2012, 3 pp.
Roberts, "Declaration Under 37 C.F.R. 1.132," Jan. 9, 2012, 3 pp.
Reinke, Corrected "Declaration Under 37 C.F.R. 1.132," May 18, 2012, 3 pp.
Roberts, Corrected "Declaration Under 37 C.F.R. 1.132," May 21, 2012, 3 pp.
International Preliminary Report on Patentability from international application No. PCT/US2010/033408, dated May 3, 2012, 10 pp.
ATMEL—T89C51CC01—Datasheet, Mar. 2003, Retrieved from the Internet on Feb. 1, 2012: URL: http://www.atmel.com/dyn/resources/prod_documents/doc3afbdd3939d4e.pdf, 10 pp.
Written Opinion of international application No. PCT/US2010/033408, dated Feb. 10, 2012, 9 pp.
Reply to Written Opinion dated Dec. 2, 2010, from international application No. PCT/US2010/033408, filed Nov. 28, 2011, 13 pp.

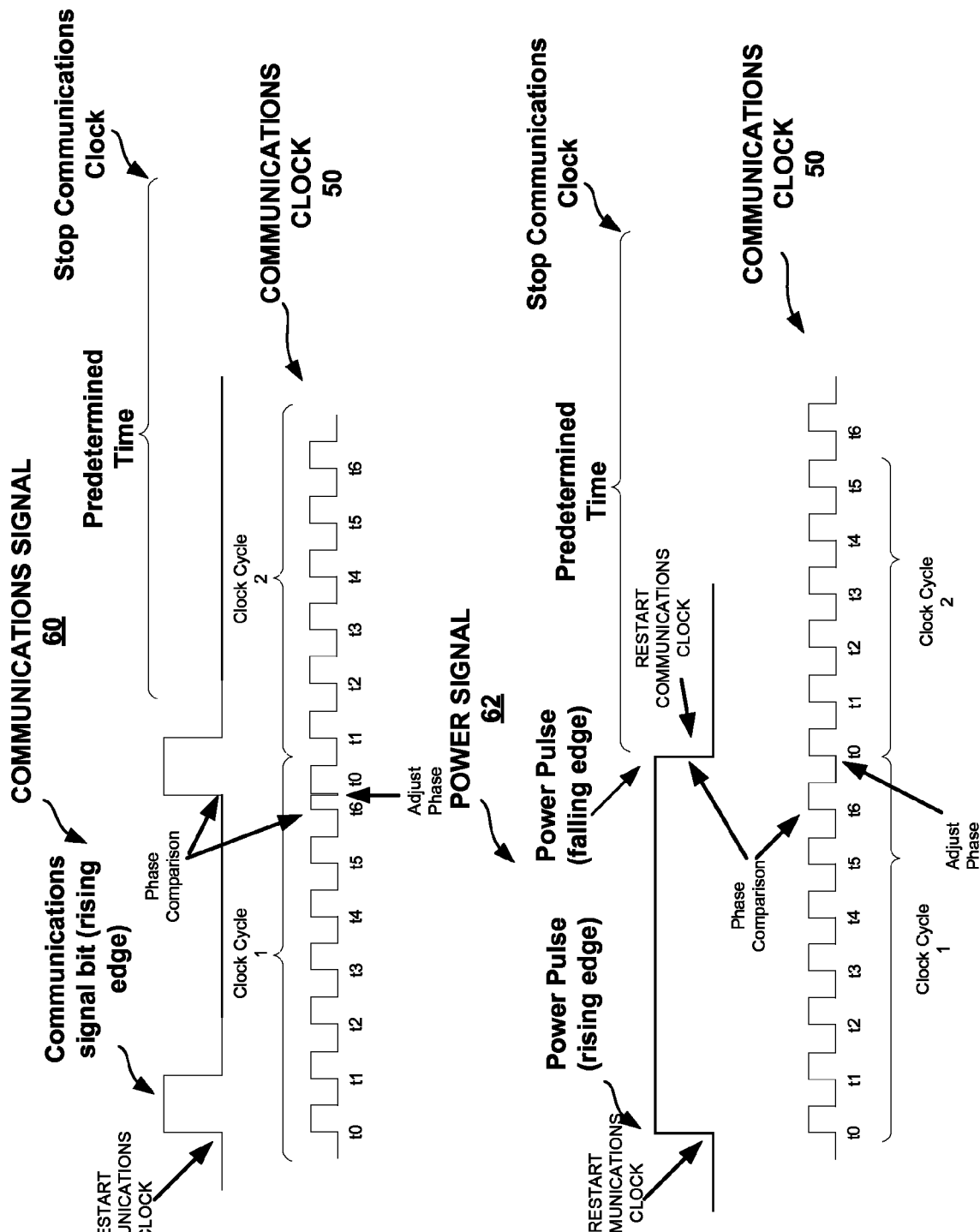

CLOCK SYNCHRONIZATION IN AN IMPLANTABLE MEDICAL DEVICE SYSTEM

TECHNICAL FIELD

This disclosure relates to implantable medical devices. More specifically, the disclosure relates to clock synchronization of one or more secondary implantable medical devices.

BACKGROUND

Some medical systems incorporate one or more implantable medical devices (IMDs). Some systems include a primary IMD, and one or more secondary IMDs. The secondary IMDs may include, for example, one or more sensors configured to collect data based on measurements taken within a patient's body. For example, secondary IMDs may include sensors that measure blood pressure, temperature, heart rate, blood composition, patient activity, or other indicators of patient health.

Because most implantable sensors are configured to be disposed within one or more structures of a patient, (e.g., the patient's heart, veins, arteries, etc.), the size and shape of such devices is a primary concern. Because of size concerns, secondary IMDs may not include an internal battery. Instead, secondary IMDs may be powered by a battery of the primary IMD. Secondary IMDs may also not include an independent accurate clock source. Thus, it may be desirable to synchronize a secondary IMD clock to a clock of a primary IMD.

SUMMARY

In general, this disclosure is directed to techniques providing for synchronization of clocks of a secondary implantable medical device (IMD). In various examples, a first clock of a secondary IMD is synchronized to one or more communications pulses received by the secondary IMD, and a second clock of the secondary IMD is synchronized to one or more power pulses received by the secondary IMD.

In one example, a method is described herein. The method includes receiving, from a primary implantable medical device (IMD), by a secondary IMD communicatively coupled to the primary IMD, at least one data pulse. The method further includes receiving, from the primary IMD by the secondary IMD, at least one power pulse. The method further includes synchronizing, by the secondary IMD, a first clock local to the secondary IMD using the at least one data pulse. The method further includes synchronizing, by the secondary IMD, a second clock local to the secondary IMD using the at least one power pulse, wherein the second clock is different than the first clock.

In another example, a system is described herein. The system includes at least one primary implantable medical device (IMD) configured to operate based on a local clock. The system further includes at least one secondary IMD communicatively coupled to the primary IMD and configured to receive at least one communication pulse and at least one power pulse from the primary IMD. The system further includes a communications clock unit configured to generate a first clock of the secondary IMD based on the at least one communication pulse. The system further includes a general purpose clock unit configured to generate a second clock different than the first clock based on the at least one power pulse.

In another example, a device is described herein. The device includes means for receiving at least one communications pulse for communicating a message. The device further includes means for receiving at least one power pulse for powering the device. The device further includes means for generating a first clock based on the at least one communications pulse. The device further includes means for generating a second clock different than the first clock based on the at least one power pulse.

In another example, a device is described herein. The device includes a communications unit configured to receive, from a primary implantable medical device (IMD), at least one data pulse and at least one power pulse. The device further includes a communications clock unit configured to synchronize a first clock local to the device based at least in part on the at least one data pulse. The device further includes a general purpose clock unit configured to synchronize a second clock local to the device different than the first clock based at least in part on the at least one power pulse.

In another example, computer-readable medium comprising instructions is described herein. The instructions are for causing a programmable processor to receive at least one communications pulse. The instructions are further for causing the programmable processor to receive at least one power pulse. The instructions are further for causing the programmable processor to generate, based on the at least one communications pulse, a first clock. The instructions are further for causing the programmable processor to generate, based on the at least one power pulse, a second clock different than the first clock.

The details of one or more examples are set forth in the accompanying drawings and the description below. Other features, objects, and advantages will be apparent from the description and drawings, and from the claims.

BRIEF DESCRIPTION OF DRAWINGS

FIGS. 3A and 3B are waveform diagrams depicting one example of synchronization of a communications clock consistent with this disclosure.

DETAILED DESCRIPTION

Figure 1:
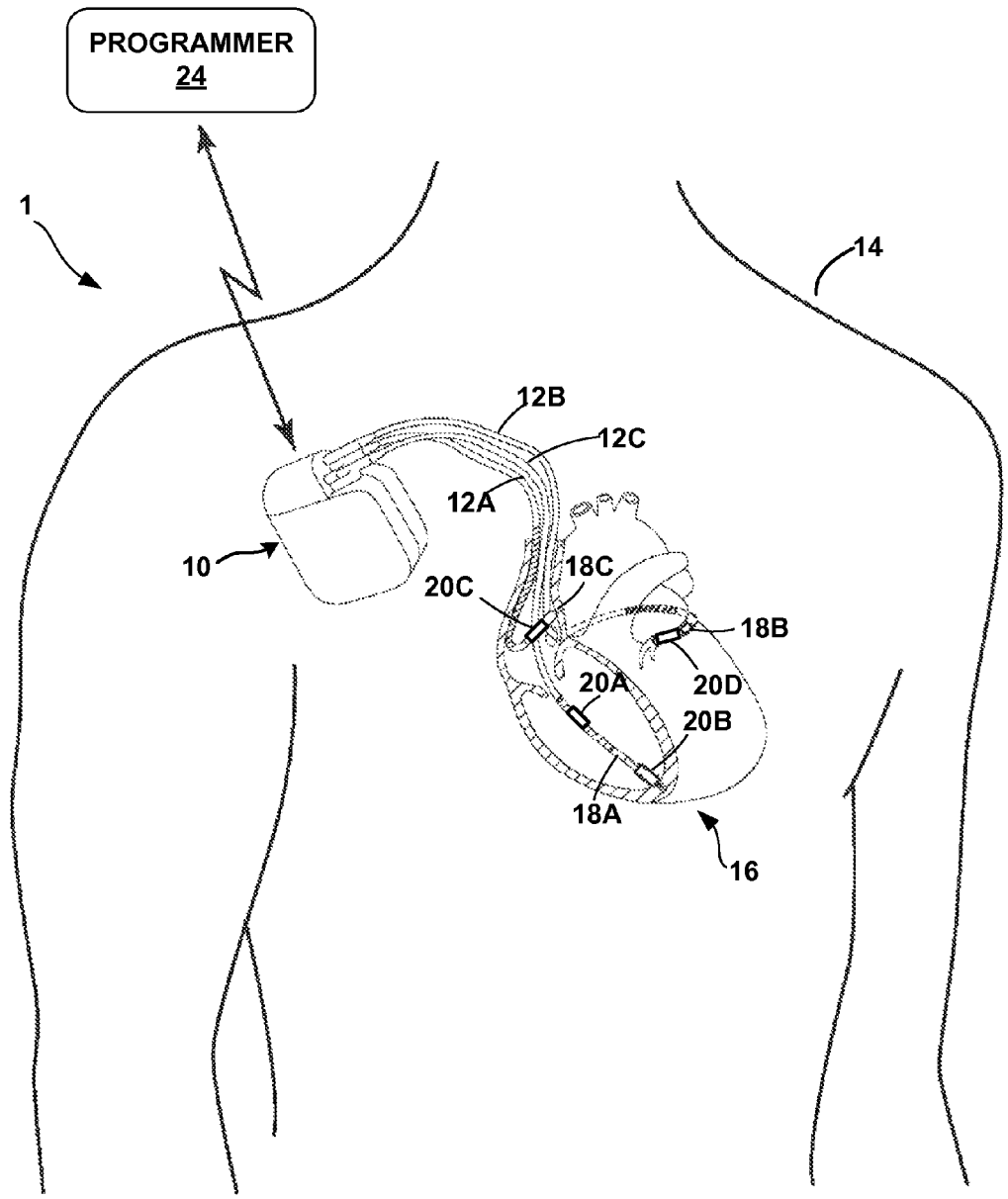
FIG. 1 is a conceptual diagram illustrating one example of an IMD system that includes a primary IMD and a plurality of secondary IMDs implanted within the body of a patient consistent with this disclosure.

FIG. 1 is a conceptual diagram illustrating one example of an IMD system 1 implanted within a patient 14 consistent with this disclosure. As depicted, system 1 includes a primary IMD 10, and a plurality of secondary IMDs 20A-20D (collectively "secondary IMDs 20"). Although the depicted example includes four secondary IMDs 20, other examples may include one or any number of secondary IMDs 20.

In the example of FIG. 1, primary IMD 10 is a cardiac stimulation device configured to deliver therapy in the form of electrical pulses to cardiac tissue. In other examples, primary IMD 10 may be configured to deliver non-cardiac therapy. For example, primary IMD 10 may be a neurostimulator configured to deliver electrical signals to one or more neurological structures of patient 14. In other examples, primary IMD 10 may be a drug delivery device configured to deliver one or more drugs or other therapeutic substances to patient 14.

The plurality of secondary IMDs 20 may include one or more sensors configured to detect one or more conditions indicative of patient 14 health. For example, the plurality of secondary IMDs 20 may include sensors configured to detect patient conditions such as blood pressure, blood flow rate, heart rate, blood makeup, substances within the blood, such as oxygen, carbon dioxide, or glucose, temperature, patient activity state (asleep, awake, exercising), or other indications of patient 14 conditions. To sense patient 14 conditions, one or more of secondary IMDs 20A-20D may employ one or more pressure sensors, blood flow sensors, force sensors, blood composition sensors, optical sensors, accelerometers, or other sensors capable of detecting patient 14 conditions. The example shown in FIG. 1 is directed to secondary IMDs 20A-20D configured to detect patient 12 conditions related to a cardiovascular system of a patient. However other types of sensors are also contemplated, such as sensors configured to detect conditions related to one or more neurological systems of patient 14.

Secondary IMDs 20 may instead or in addition be configured such as actuators, e.g., configured to take some action, such as delivery of a cardiac, neurological, electrical stimulation, drug, or other therapy. For example, a secondary IMD 20 may be a drug delivery device configured to deliver a drug to patient 14. In other examples, primary IMD 10 may be the drug delivery device, and a secondary IMD 20 may include one or more sensor elements configured to detect conditions of a drug delivery device, e.g., whether the drug delivery device has administered a drug to patient 14. In other examples, a secondary IMD 20 may be a neurostimulator or similar device configured to deliver electrical stimulus to one or more neurological structures of a patient, or a sensor configured to monitor a neurostimulator, including therapy delivered by the neurostimulator.

As also shown in FIG. 1, secondary IMDs 20 are electrically coupled to primary IMD 10. Secondary IMDs 20A-20D may be coupled to primary IMD 10 via one or more leads 12A-12C. Leads 12A-12C may carry one or more electrodes 18A-18C for the delivery of electrical therapy to one or more cardiac tissues (e.g., heart 16), one or more neurological structures, or one or more other structures of a patient. In other examples not depicted, secondary IMDs 20 may be coupled to primary IMD 10 via one or more non-lead conductors. In still other examples not depicted, one or more of the plurality of secondary IMDs 20 may be wirelessly coupled to primary IMD 10, for communications, power delivery, or other purposes.

The example medical system 1 depicted in FIG. 1 further includes programmer 24. Programmer 24 may be configured to communicate with one or more of primary IMD 10 or secondary IMDs 20. Programmer 24 may be configured to communicate with one or more of IMDs 10 and/or 20 via wireless communication such as RF telemetry. Programmer 24 may be configured to communicate with IMDs 10, 20 to access data detected by any of IMDs 10 and 20. Programmer 24 may be configured to update therapy parameters or operational software of any of IMDs 10 and 20. Programmer 24 may further be configured to power any of IMDs 10 and 20, for example by inductively coupling power to any of IMDs 10 and 20.

Figure 2:
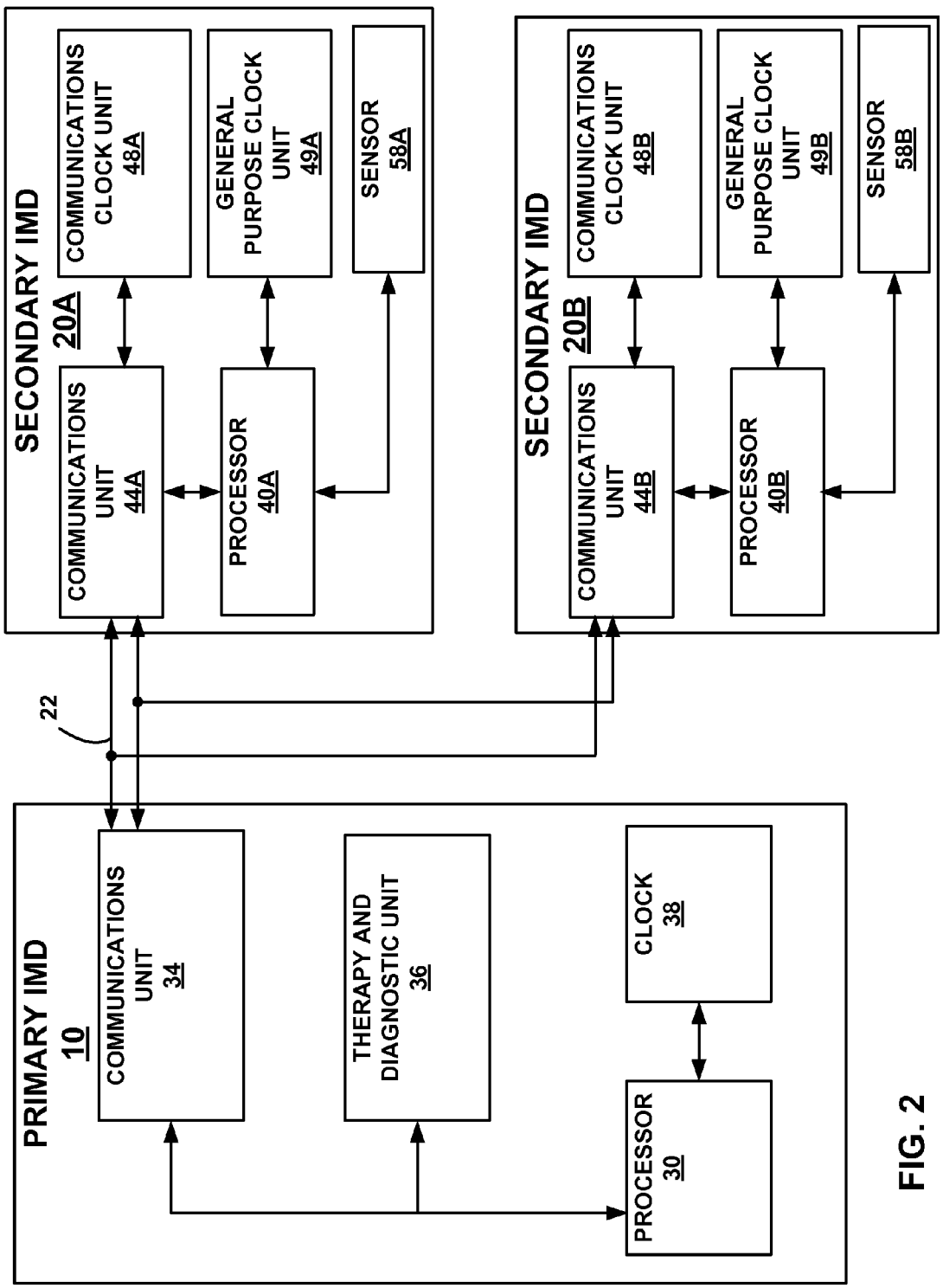
FIG. 2 is a block diagram illustrating components of a primary IMD and secondary IMDs coupled to the primary IMD consistent with this disclosure.

FIG. 2 is a block diagram illustrating components of a primary IMD 10 and multiple secondary IMDs 20A and 20B (collectively "secondary IMDs 20") coupled to primary IMD 10 via a system bus 22 consistent with this disclosure. As discussed above with respect to FIG. 1, system bus 22 may be carried by one or more leads (e.g., leads 12A-12C of FIG. 1) carrying electrodes for sensing of electrical signals within patient 14 and/or the delivery of electrical stimulation to patient 14 tissues. System bus 22 may comprise conductors coupled to the electrodes and/or dedicated conductors coupled to secondary IMDs 20.

As depicted in FIG. 2, primary IMD 10 includes a processor 30. Processor 30 may be configured to control operations of primary IMD 10. Processor 30 may execute computer-readable instructions stored in one or more memories of primary IMD 10 to control operations of primary IMD 10. For example, processor 30 may be operative to control a communications unit 34. Communications unit 34 may be operable to communicate with programmer 24 and/or one or more secondary IMDs 20. Processor 30 may further be operable to control a therapy and diagnostic unit 36 configured to process and/or detect patient or other conditions, and/or to deliver therapy to the patient. Processor 30 may operate based on a local clock 38. In one example, local clock 38 is a highly accurate clock. In many IMD applications, the critical nature of timing electrical signals delivered to patient tissue (pacing, defibrillation, neurological stimulation) may require a local clock of primary IMD 10 to be highly stable. In one example, local clock 38 is based on one or more crystal oscillators.

As shown in FIG. 2 communications unit 34 is coupled to a system bus 22. System bus 22 may be any type of known conductor configured to operate as a conduit for transmission of electrical signals. In the example depicted in FIG. 2, system bus 22 is a two-wire bus. As depicted above in FIG. 1, system bus 22 may be carried by one or more leads 12A-12C of medical device system 1.

Also depicted in FIG. 2 are two secondary IMDs 20A and 20B. Secondary IMDs 20 may include sensor elements 58A-58B (collectively "sensor elements 58") of IMD system 1. Secondary IMDs 20 may instead or in addition include components configured to deliver therapy to a patient, for example electrical therapy or drug delivery therapies. Secondary IMDs 20 may include one or more sensor elements 58, for example pressure sensors, temperature sensors, or other sensors configured to detect patient conditions.

The one or more sensor elements 58 of secondary IMDs 20 may be configured to detect patient conditions and produce corresponding signals indicative of those conditions in an analog format. Secondary IMDs 20A and 20B may include one or more digital processing circuits, for example one or more analog to digital converters (ADCs), configured to translate one or more analog signals indicative of detected patient conditions and translate them to digital signals for processing by the respective processor 40A or 40B (collectively "processors 40"), for communication to primary IMD 10, or for any other purpose where a digital representation of sensed data is desirable.

As depicted in FIG. 2, secondary IMDs 20A and 20B each include a respective communications unit 44A, 44B (collectively "communications units 44") coupled to system bus 22. Communications units 44 may be operable to receive communication signals from communications unit 34 of primary IMD 10 via system bus 22. Communications units 44 may further be operable to transmit one or more communications signals to primary IMD 10 via system bus 22.

Communications units 44 may further be operable to receive power signals from communications unit 34 of primary IMD 10 via system bus 22. Communications units 44 may be operable to extract energy from received power signals and convert the extracted energy into electrical energy to power components of secondary IMDs 20, for example processor 40, or one or more sensor elements 58 included in secondary IMDs 20. Communications units 44 may include one or more circuit elements, such as a rectifier circuit, to convert received power signals to DC waveforms suitable for charging an energy storage element. Power signals communicated by primary IMD 10 via system bus may be single pulses, biphasic pulses, or bursts of power pulses. The power signals may be communicated according to one or more time intervals based on a local clock of primary IMD 10.

In one example, power pulses may be distinguishable from data pulses based on a pulse amplitude. For example, an amplitude of a power pulse may be greater than an amplitude of a data pulse. Power pulses as discussed herein may not necessarily be utilized to transmit power to secondary IMD 20. Power pulses as discussed herein may include any pulse transmitted by primary IMD 10 with an amplitude greater than a data pulse amplitude. In one example, a power pulse may have an amplitude that is an order of magnitude greater than an amplitude of a data pulse.

As depicted in FIG. 2, communications units 44 are a single unit configured to receive both communications signals and power signals from primary IMD 10. In other examples not depicted, communications units 44 may be comprised of distinct, separate components, for example a first component for receipt and/or processing of communications signals and a second component for receipt and/or processing of power signals from primary IMD 10.

In one example where the same component is configured to receive both communication and power signals, the component may include one or more electrical circuits (e.g., a voltage comparator) to compare a voltage level of a received pulse to one or more thresholds to distinguish between communications and power pulses received via system bus 22.

Secondary IMDs 20A and 20B of FIG. 2 also include clock units 48A-48B and 49A-49B. Each of clock units 48A-48B and 49A-49B may be operative to generate distinct clocks signals utilized for different purposes by secondary IMDs 20. For example, clock unit 48A-48B may be configured to generate a communications clock utilized for communications functions of secondary IMDs 20A and 20B. Communications clock units 48A-48B (collectively "communications clock units 48") may be configured to generate clocks that are operative only during times when a communications signal is received from primary IMD 10 and/or transmitted to primary IMD 10.

Communications clock units 48 may be configured such that, when a first bit of a message from primary IMD 10 is received, the communications clock unit 48 may operate to initialize the communications clock. Communications clock units 48 may continue to generate clock pulses while the message is being received or transmitted, e.g., while bits of the message are being transferred between primary IMD 10 and secondary IMDs 20 via system bus 22. A communications clock unit 48 may be configured to stop generating the communications clock once a predetermined time has passed since a rising edge of a communications pulse was last detected by the respective communications unit 44.

It may be advantageous for communications clock units 48 to operate the communications clocks in the manner described above, because secondary IMDs 20 may not include an internal battery to power the secondary IMDs. Instead, secondary IMDs 20 may be configured to receive, via power signals communicated via system bus 22, power for device operation. Thus, it may be advantageous to minimize an amount of power consumed by secondary IMDs 20 by limiting the communications clock generated by communications clock units 48 such that communications clock units 48 only generate the communications clock at necessary times when a communications signal is being transmitted or received by communications units 44.

As discussed above, each of secondary IMDs 20A-20B also includes a general purpose clock unit 49A-49B. General purpose (GP) clock units 49A-49B (collectively "GP clock units 49") may be operative to generate a GP clock for use by non-communicative functions of secondary IMDs 20. For example, one or more sensor elements 58 of secondary IMDs 20 may be configured to sample patient conditions according to predetermined time intervals. The one or more predetermined time intervals may be based upon the GP clock generated by a GP clock unit 49. As will be described later, GP clock unit 49 may be constantly running while secondary IMD 20 is operating.

In other examples, the GP clock may be utilized to identify a duration of a power on reset signal of secondary IMDs 20. In still other examples, the GP clock may be utilized to access information stored in one or more memory components (e.g., a non-volatile Flash memory) of secondary IMDs 20. For example, the GP clock may be utilized to access trim codes that quantify one or more offset values that compensate for variations in sensor elements 58 of secondary IMDs 20, for example to calibrate a pressure or temperature sensor elements.

As described herein, a GP clock of secondary IMDs 20 may be synchronized to a clock local to primary IMD 10 based on receipt of power pulses transmitted by primary IMD 10. Synchronization of a GP clock of secondary IMDs 20 to a clock local to primary IMD 10 may present various beneficial aspects. For example, the GP clock synchronization discussed herein may allow for more accurate processing and/or analysis of measurements detected by one or more sensors of a secondary IMD 20 with other measurements detected by primary IMD 10 and/or other secondary IMDs 20. In another example, the GP clock synchronization discussed herein may allow for improved allocation of memory space in either of primary IMD 10 or secondary IMDs 20, because an amount of data collected by one or more sensors of secondary IMDs 20 is more predictable. In another example, secondary IMDs 20 may include one or more filter components, e.g., a low pass filter, to remove noise from one or more signals indicative of detected measurements. According to this example, a low pass filter may be selected with a static filter value based on a known frequency of detected measurements, making the filter more accurate and/or eliminating a need for a variable frequency filter to achieve a similar level of filter accuracy.

Components of primary IMD 10 and secondary IMDs 20A-20B are described with respect to FIG. 2 as separate components included within IMDs 10 and 20A-20B. However, various other configurations of these components are also contemplated. For example, one or more of a communications unit 44, processor 40, communications clock unit 48, GP clock unit 49, sensor elements 58, digital processing circuitry (e.g., ADC), memories, or any other component of a primary IMD 10 and/or secondary IMD 20 may be combined in one or more integrated components, such as a single Application Specific Integrated Circuit (ASIC), Field Programmable Gate Array (FPGA), or other form of computing device. Specifically, in one example, a processor 40 may be integrated in the same computing device as one or more circuits of a communications unit 44.

FIGS. 3A and 3B are a conceptual diagrams depicting one example of synchronization of a communications clock 50 of a secondary IMD 20. According to the example depicted in FIG. 3A, communications clock 50 may be formed of a series of clock cycles. The clock cycles consist of a predefined number of clock pulses, e.g., seven clock pulses in the example of FIGS. 3A and 3B. For this purpose, communications clock unit 48 may incorporate one or more counter modules configured to provide a count from 1-7 (or 0-6). As depicted, a communications unit 44 may be configured to detect a rising edge of communications signal 60 from primary IMD 10. Upon detection of the rising edge, the communications clock unit 48 may be configured to initiate a first clock cycle (clock cycle 1 in FIG. 3).

In one example, each time a rising edge of a communications signal 60 pulse is detected, the communications clock unit 48 may reset communications clock 50 (e.g., by resetting the above-described counter to a value of 0), to generate a new clock cycle starting at phase t0. The new clock cycle may be generated a short time before, after, or during pulse t6. The new clock cycle may also be generated a short time before, after, or during any other pulse of communications clock 50, e.g., pulse t5. In one example, the new clock cycle may also be generated a short time before, after, or during one or more pulses subsequent to pulse t6 (e.g., a t7 pulse or a t8 pulse).

The generation of a new clock cycle, may depend on when the communications is received. As illustrated in FIG. 3B, communications clock unit 48 may in addition or instead be configured to reset communications clock 50 to pulse t0 based on detection of a rising or falling edge of a power signal 62 received from primary IMD 10. The example of FIG. 3B shows the communications clock 50 reset to pulse t0 in response to detection of a falling edge of a power pulse of power signal 62. Restarting communications clock 50 based on detection of a rising edge of a data bit of communications signal 60, or a rising or falling edge of a power pulse of power signal 62 may be advantageous, because doing so may help to insure that the start of each clock cycle of communications clock 50 is phase locked to a clock of primary IMD 10.

As also depicted in FIGS. 3A and 3B, communications clock unit 44 may perform a phase comparison upon receipt of a communications or power pulse. For example, as depicted in FIG. 3A, upon receipt of a communications pulse, a phase comparison may be performed between a rising edge of the t6 pulse (of clock cycle 1 in FIG. 3A) and a rising edge of the communications pulse. In another example, as depicted in FIG. 3B, a phase comparison may be performed between the t6 pulse and a rising or falling edge of a received power pulse (falling edge in the FIG. 3B example). FIG. 3B shows one example in which the communications clock is too fast, as the t6 pulse rising edge occurs before the falling edge of the power pulse).

In one example, if communications clock 50 is synchronized with one or more data and/or power pulses, the t6 pulse may be non-existent, or may be a very narrow pulse in comparison to pulses t0-t5 of the communications clock 50. In one example, if communications clock 50 is synchronized with one or more data and/or power pulses, an operative edge (rising or falling) of the communications or power pulse may occur substantially at the same time as a falling edge of the t5 pulse of communications clock 50. According to this example, the t6 pulse would not exist, and instead a new clock cycle (e.g., clock cycle 2), would be started a short time after a falling edge of the t5 pulse.

To compare phases as described above, a communications clock unit 44 may include one or more circuits configured to perform the phase comparison and generate a voltage signal which represents a difference in phase between two signal inputs, e.g., one or more phase frequency detectors, frequency mixers, or analog multiplier circuits. If a phase comparison indicates that an edge of a received communications or power pulse occurs before a rising edge of pulse t6 (or a falling edge of pulse t5) of the first clock cycle, then communications clock 50 is too slow. In the alternative, if the phase comparison indicates that an edge of a received communications or power pulse occurs after a rising edge of pulse t6, then communications clock 50 is too fast.

To compensate for any detected phase discrepancy between the first and second clock cycles, a communications clock unit 48 may include one or more clock trims, e.g., fine clock trims. The clock trims may be digital trims values for adjustment of a phase of the communications clock 50. The digital trim values may be stored on one or more memories, e.g., SRAM memory, register, or a Flash memory, of the secondary IMD 20. The clock trims may be applied to delay pulses of communications clock 50 or to speed up pulses of communications clock 50 such that communications clock 50 is substantially in phase with a received communications or power pulse. The communications clock unit 48 may include one or more circuits configured to perform the phase comparison digitally. Results of one or more phase comparisons may be stored in one or more memories. In one example, communications clock unit 48 may determine one or more digital trim values to utilize for adjustment of a phase of the communications clock 50 based on the results of a plurality of phase comparisons stored in the one or more memories. In one example, digital trim values are updated one bit at a time based on one or more phase comparisons.

Figure 4A:
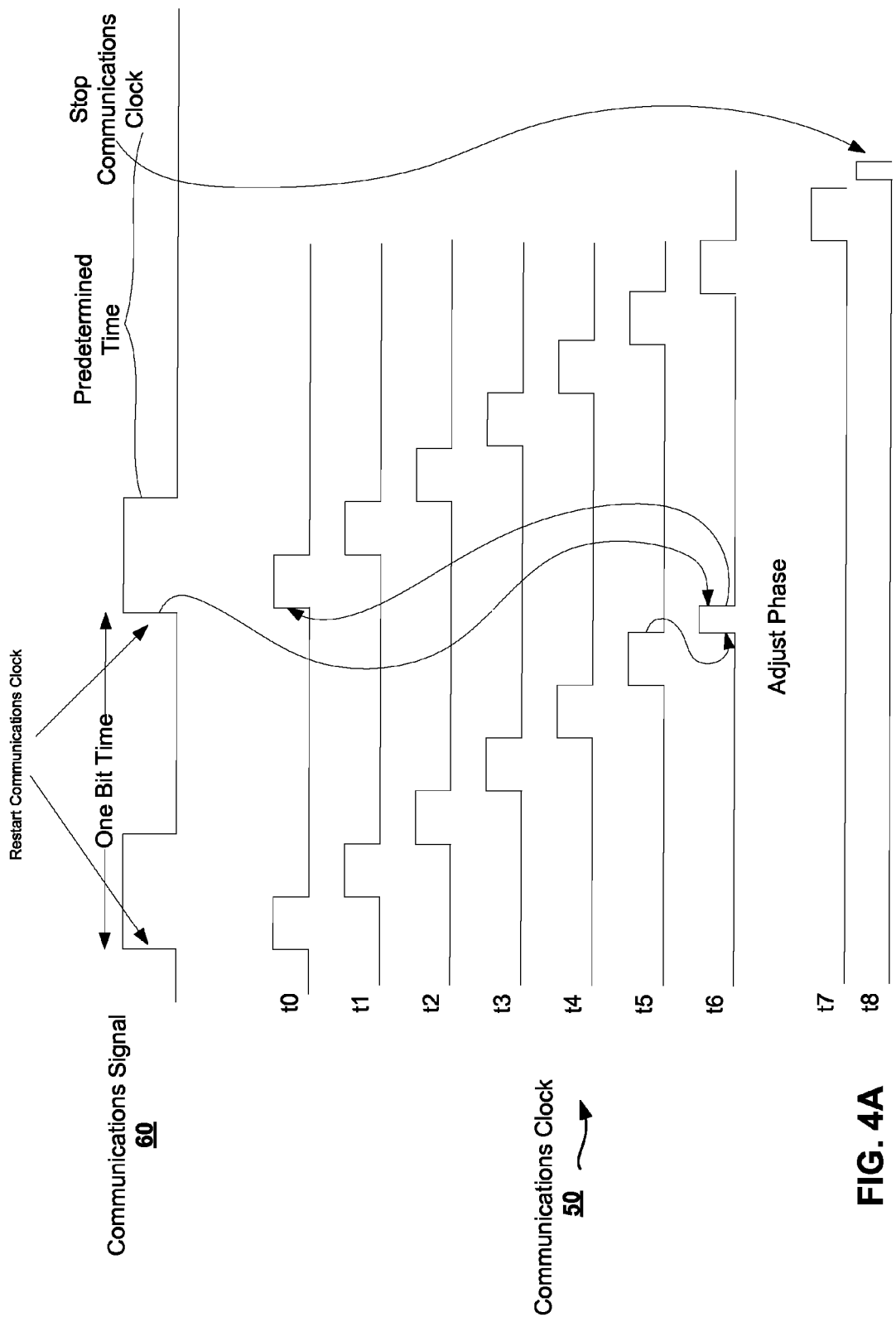
FIGS. 4A and 4B are waveform diagrams depicting one example of synchronization of a communications clock consistent with this disclosure.
Figure 4B:
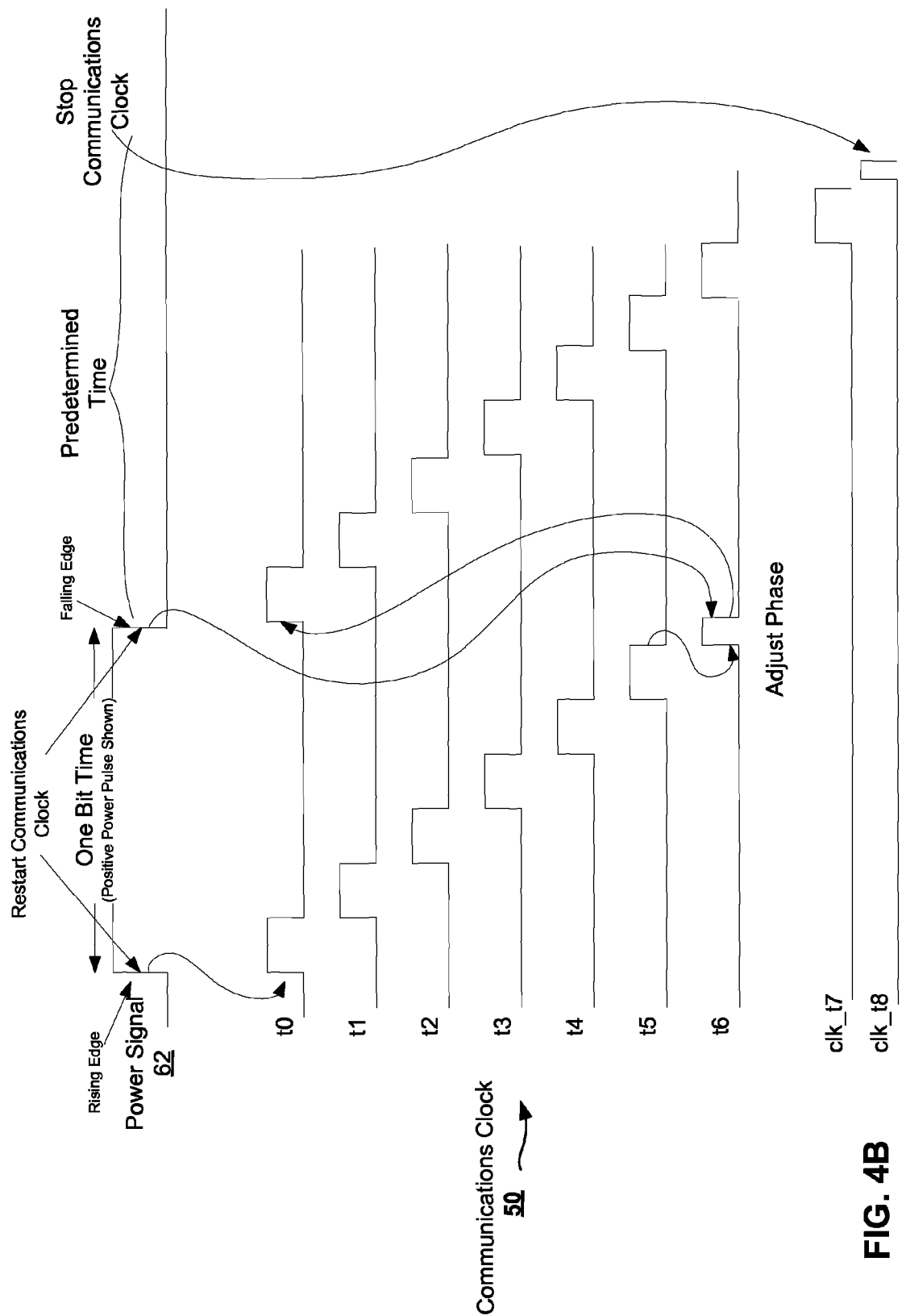

FIGS. 4A and 4B depict alternative examples of synchronization of a communications clock 60. The example of FIG. 4A shows synchronization of a communications clock 50 based on receipt of communications pulses of a communications signal 60. According to the depicted example, communications clock unit 44 may include a delay chain consisting of multiple delay elements cascaded in series in place of the clock and counter described above. Each delay element may be used to create one of the clock pulses. When a new clock cycle begins (initiated by a rising edge of a communications clock 60 pulse), t0 is set, and delay t0 is triggered. When delay_t0 times out, t0 is cleared, t1 is set, and delay t1 is triggered. The pulse may continue to propagate through the cascade of delays creating each of the clock pulses in turn, e.g., t0, t1, t2, t3, t4, t5, t6, t7, t8. When a rising edge of a communication pulse is detected, a phase comparison as described above may be performed. If communications clock 50 is synchronized with detected pulses of communications signal 60, each of clock pulses t0-t6 may have substantially equal widths.

The phase comparison may indicate that a rising edge of the communications pulse occurs before or after a rising edge of clock pulse t6. The phase comparison may be latched. A phase of one or more clock pulses may be adjusted (e.g., via one or more clock trim values as discussed above), and clock pulse t0 may be initiated, beginning the cascade of delays again. The example of FIG. 4 shows communications clock 60 running fast with respect to a received pulse of communications signal 50, i.e., a rising edge of clock pulse t6 occurs before a rising edge of a detected communications pulse of communications signal 60.

FIG. 4B depicts one example of synchronization of a communications clock 50 similar to the example depicted in FIG. 4A, except communications clock 50 is synchronized to a rising and/or falling edge of pulses of a received power signal 62. According to this example, the above-described reset and phase adjustment may be initiated by a rising or falling edge of a power pulse (falling edge in FIG. 4B).

As discussed above, communications clock 50 may be synchronized (e.g., restart communications clock signal at t0) upon receipt of either a rising edge of a communications pulse of communications signal 60 or a rising or falling edge of a power pulse of power signal 62. Using either of communications or power pulses to synchronize communications clock 50 may be advantageous, because it allows for synchronization of communications clock 50 at times when communications are not being received or transmitted by the secondary IMD 20.

For example, upon power up, primary IMD 10 may transmit a series of power pulses to a secondary IMD 20. The power pulses may be utilized to charge one or more energy storage elements (e.g., capacitive elements) of the secondary IMD 20. The power pulses may further be utilized to synchronize a GP clock of the secondary IMD 20, which may be used for various initialization procedures, e.g., to read out sensor trim values from a memory of the secondary IMD 20 and calibrate sensors 58 for measurement, among other functions of secondary IMD 20.

In one example, power pulses received at power up may be used to synchronize a communications clock 50 of a secondary IMD 20. Although communications clock 50 typically does not run when messages are not being communicated with primary IMD 10, the communications clock may run for a short period of time (e.g., one or two clock cycles as described above) after detection of a rising or falling edge of a pulse of power signal 62. The above-described phase comparison between a phase of a t6 bit of the communications clock 50 and a detected rising or falling power pulse edge may be performed, and a phase comparison value (trim value) may be stored in memory (or a register or other memory element) for later use. Upon subsequent receipt of a communication pulse of a communication signal 60, the stored phase comparison value may be utilized to initialize the communications clock 50, for example to determine a frequency of pulses of the first clock cycle depicted in FIGS. 3A and 3B. The above described storage of phase comparison values may further be utilized at times other than power up, for example where a secondary IMD 20 is awakened from a standby mode for communications with primary IMD 10. Similarly, phase comparison values stored in memory based on power pulses received during the standby mode may be utilized to initialize communications clock 50.

As discussed above, a communications clock 50 may be operated intermittently in order to reduce an amount of power consumed by a secondary IMD 20. As illustrated in FIG. 3A, a secondary IMD 20 (e.g., a communications clock unit 48 of a secondary IMD 20 as illustrated in FIG. 2) may be operable to stop generation of communications clock 50 (stop generating subsequent clock pulses/cycles of communications clock 50), a predetermined time after receipt of a rising edge of a communications pulse of communications signal 60. As illustrated in FIG. 3B, a secondary IMD 20 may be operable to stop generation of communications clock 50, a predetermined time after receipt of a rising or falling edge of a power pulse of power signal 62 (falling edge in FIG. 3B). The predetermined time after receipt of the rising edge of a communications signal bit may or may not be the same as the predetermined time after receipt of a falling edge of a power pulse of power signal 62.

Figure 5:
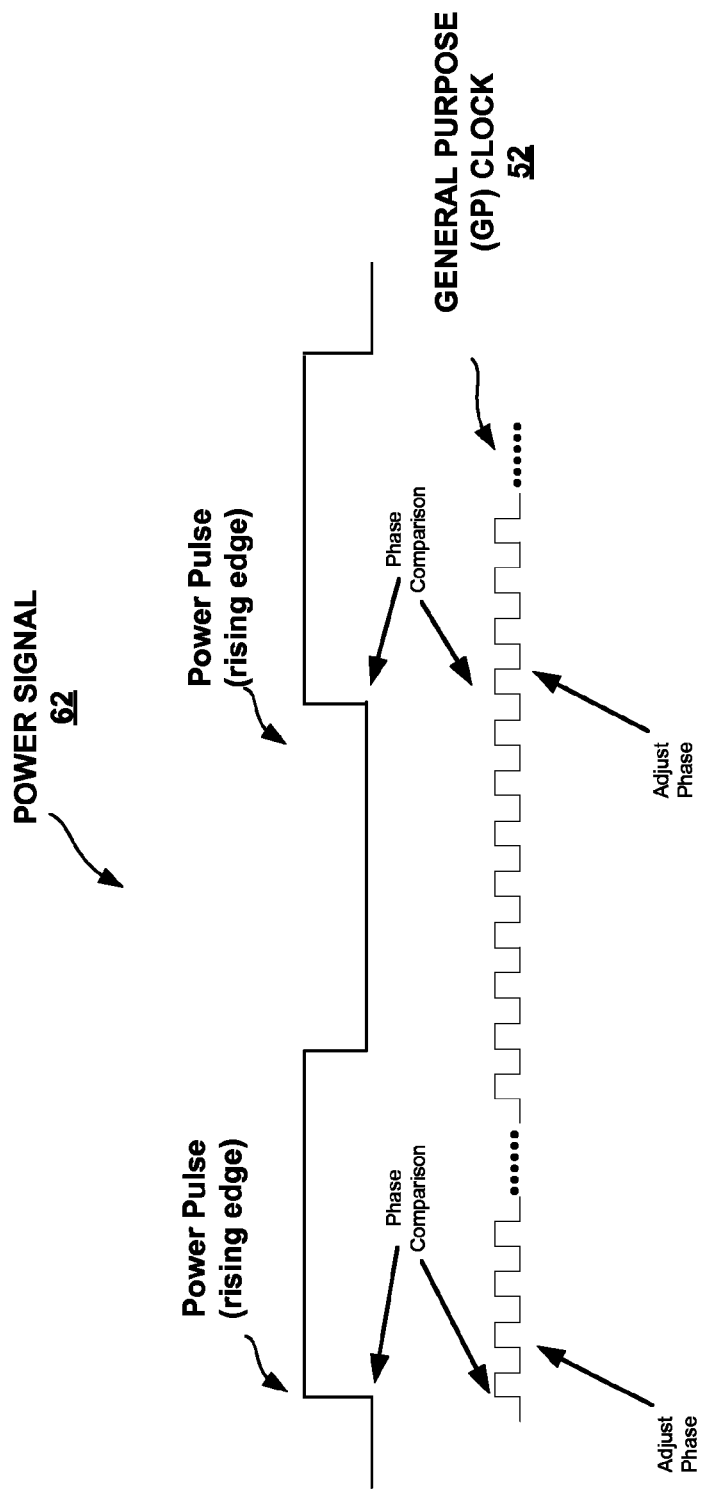
FIG. 5 is a waveform diagram depicting one example of synchronization of a general purpose (GP) clock consistent with this disclosure.

FIG. 5 is a conceptual diagram depicting one example of synchronization of a general purpose (GP) clock 52 of a secondary IMD 20. Unlike communications clock 50 depicted in FIGS. 3A and 3B, the GP clock 52 may be constantly running while the secondary IMD 20 is operating, e.g., the GP clock 52 may not be operated intermittently like communications clock 50 depicted in FIGS. 3A and 3B.

As depicted in FIG. 5, a phase comparison between GP clock 52 and a received power pulse of power signal 62 may be performed each time a rising edge of a power pulse is detected. Although not depicted in FIG. 5, a phase comparison between GP clock 52 and a received power pulse of power signal 62 may instead or in addition be performed each time a falling edge of a power pulse is detected. As discussed above with respect to communications clock unit 48, a general purpose clock unit 49 may include one or more components, e.g., electrical circuitry, to perform the phase comparison (e.g., a phase comparator circuit). As also discussed above with respect to a communications clock unit 48, a general purpose clock unit 49 may employ one or more digital trim values and associated circuitry configured to adjust the GP clock 52 signal based on the phase comparison.

Figure 6:
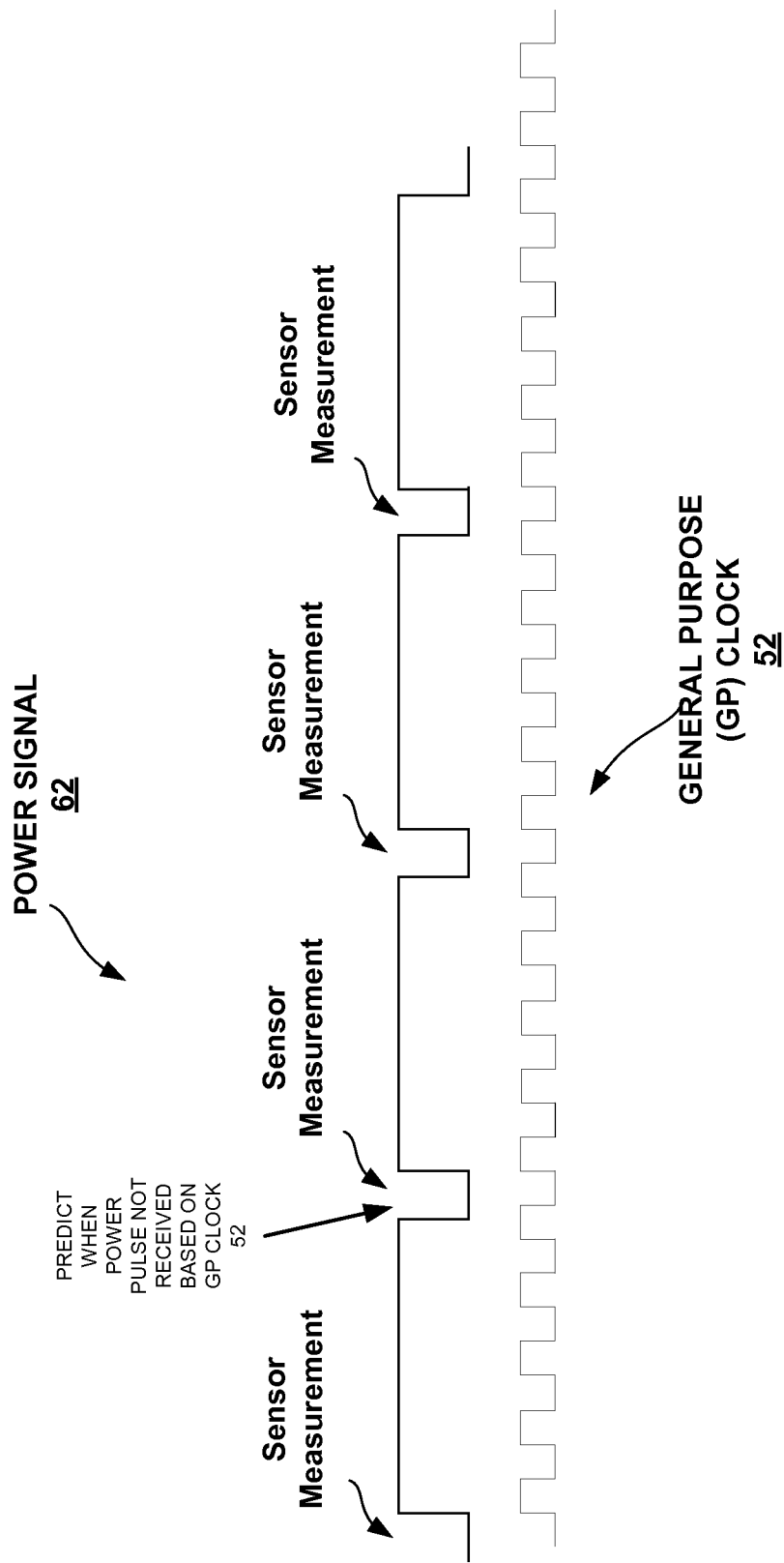
FIG. 6 is a waveform diagram depicting operation of a sensor of a secondary IMD to detect patient conditions consistent with this disclosure.

In one aspect, synchronizing a GP clock 52 of a secondary IMD 20 may be advantageous, because it may allow for improved sensor 56 measurement without interference resulting from received pulses of power signal 62. For example, as discussed above, and as depicted in FIG. 6, GP clock 52 of a secondary IMD 20 may be utilized to determine intermittent detection times for a sensor or sensors 58 of a secondary IMD 20. Operating sensors of a secondary IMD 20 intermittently as depicted in FIG. 5 may have certain benefits, such as reducing a level of power consumed by the measurements. Because synchronization of the GP clock 52 to a phase of the power pulses of power signal 62 as depicted in FIG. 5 above enables prediction of power pulse timing, sensor 56 measurements may be taken at intervals where a power pulse is not expected to be received. To state it another way, one or more sensors 56 may be turned off during arrival of one or more power pulses based on whether the one or more pulses are expected to be received. By doing so, one or more sensors of a secondary IMD 20 may perform measurements of patient conditions without interference due to noise caused by power pulses of power signal 62.

In one example, the one or more sensors of secondary IMD 20 may be operative to sample sensed data at a fixed rate. The fixed rate may be selected such that, if GP clock 52 is synchronized with the one or more power pulses as described herein, the sensor only detects data when one or more power pulses is not expected to be received, e.g., in between receipt of sequential power pulses. According to this configuration, sensor operation to detect patient conditions may be "turned off," or not operated to detect patient conditions, during time periods where receipt of a power pulse is expected. Thus, the sensor may be configured to detect patient conditions during time periods of little or no noise caused by the receipt of power pulses.

In one example, a sensor (e.g., a capacitive pressure sensor) may be configured to sample, (e.g., detect patient conditions), at a continuous fixed rate of 4 kHz. If power pulses are transmitted based on 250 us intervals, the operation of the sensor at the 4 kHz frequency may cause the sensor detection to line up with intervals between successive power pulses.

In one example, GP clock unit 49 may be configured to define a frequency lock period after initialization of the GP clock 52, or when GP clock 52 has lost synchronization (lock). Following the frequency lock period, GP clock unit 49 may be configured to determine, based on the currently operating GP clock 52, a phase/frequency error between a rising or falling edge of a received power pulse and the GP clock 52. Accordingly, one or more digital trim values as discussed above may be utilized to synchronize the GP clock based on the detected phase/frequency error.

The examples described herein directed to synchronizing communications clock 50 and GP clock 52 based on received communications and/or power pulses are provided for exemplary purposes only. One of ordinary skill in the art will recognize that other methods of synchronizing multiple clocks of a secondary IMD based on receipt of data and/or power pulses are also contemplated and consistent with this disclosure. Furthermore, FIGS. 3A-3B, FIGS. 4A-4B and FIGS. 5-6 include depictions of relationships between received pulses and clocks synchronized to those pulses. These depictions are provided for exemplary purposes only to explain interrelationships between received communication and/or power pulses and clocks as described herein. One of ordinary skill in the art will recognize that other configurations are also contemplated, e.g., faster or slower clock or pulse speeds, and/or relationships between power and/or data pulses and the respective clocks discussed herein.

As described herein, synchronization of GP clock of secondary IMD 20 to a clock local to primary IMD 10 (e.g., a crystal clock of primary IMD 10) based on receipt of power pulses transmitted by primary IMD 10 may provide various advantages. For example, GP clock 52 synchronization may allow for more accurate processing and/or analysis of measurements detected by one or more sensors 58 of a secondary IMD 20 with other measurements detected by primary IMD 10 and/or other secondary IMDs 20 (e.g., ECG, EKG waveforms detected by primary IMD 10). In another example, GP clock 52 synchronization discussed herein may allow for improved allocation of memory space in either of primary IMD 10 or secondary IMDs 20, because an amount of data collected by one or more sensors of secondary IMDs 20 is more predictable. In another example, secondary IMDs 20 may include one or more filter components, e.g., a low pass filter, to remove noise from one or more signals indicative of detected measurements. According to this example, a low pass filter may be selected with a static filter value based on a known frequency of detected measurements, making the filter more accurate and/or eliminating a need for a variable frequency filter to achieve a similar level of filter accuracy.

Figure 7:
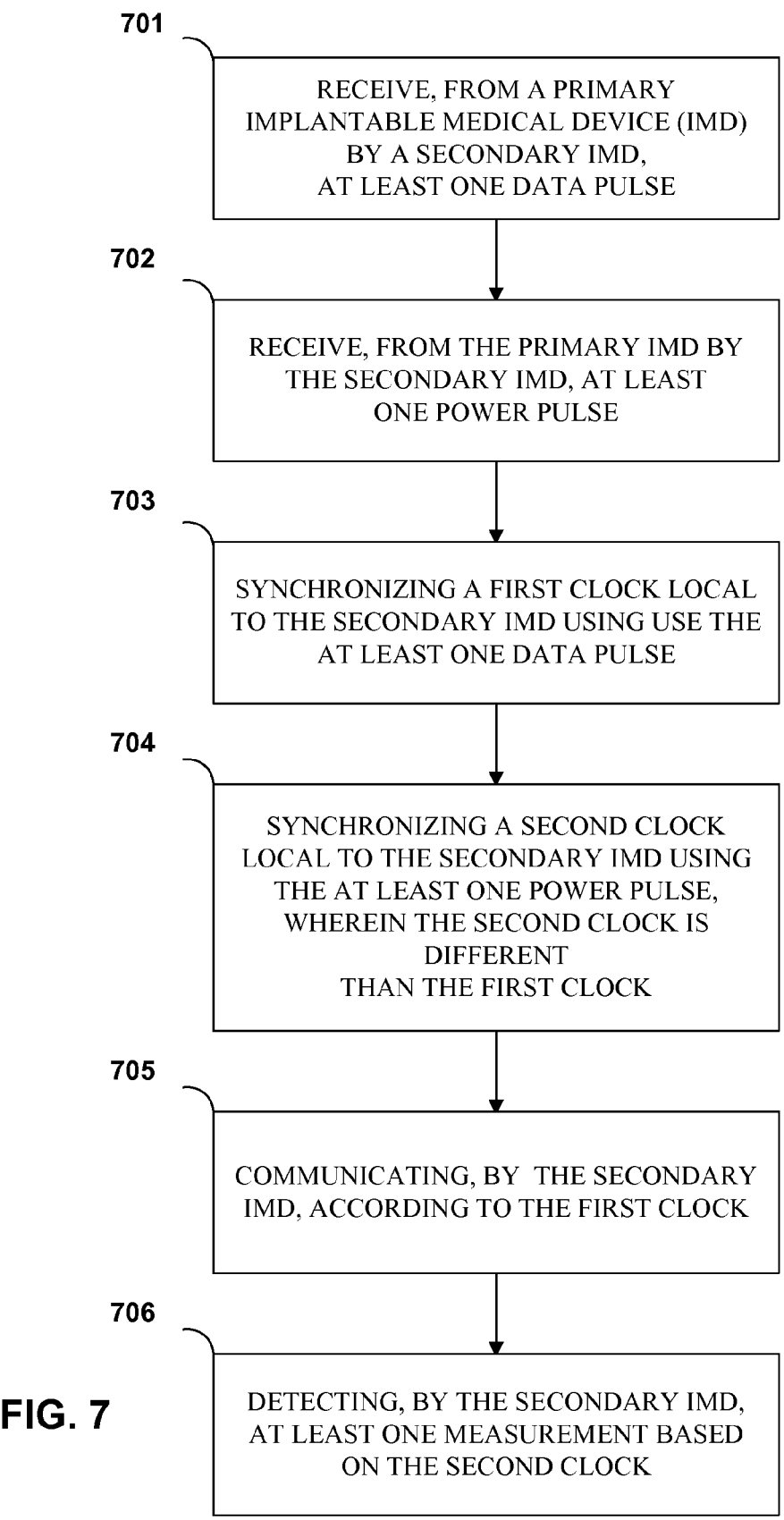
FIG. 7 is a flow chart diagram depicting one example of a method of synchronizing clocks of a secondary IMD consistent with this disclosure.

FIG. 7 is a flow chart diagram depicting one example of a method of synchronizing clocks of a secondary IMD consistent with this disclosure. The method includes receiving, from a primary implantable medical device (IMD) 10 by a secondary IMD 20, at least one data pulse (701). The method further includes receiving, from the primary IMD 10 by the secondary IMD 20, at least one power pulse (702). The method further includes synchronizing a first clock 50 local to the secondary IMD 20 using the at least one data pulse (703). The method further includes synchronizing a second clock 52 local to the secondary IMD 20 using the at least one first power pulse (704). The method further includes communicating, by the secondary IMD 20, according to the first clock 50 (705). The method further includes detecting, by the secondary IMD, at least one measurement based on the second clock (706). In one example, the method may further include using the at least one power pulse to synchronize the first clock 50 local to the secondary IMD 20.

In one example, the at least one power pulse is a first at least one power pulse, and the method may include estimating, based on the second clock 52, an arrival time of at least one subsequent power pulse, and detecting, via at least one sensor 58 of the secondary IMD 20, at least one condition based on an estimated arrival time of the at least one subsequent power pulse. In one example, detecting at least one condition based on an estimated arrival time of the at least one subsequent power pulse includes turning off at least one detection operation of the at least one sensor 58 during arrival of the at least one subsequent power pulse based on the estimated arrival time.

Figure 8:
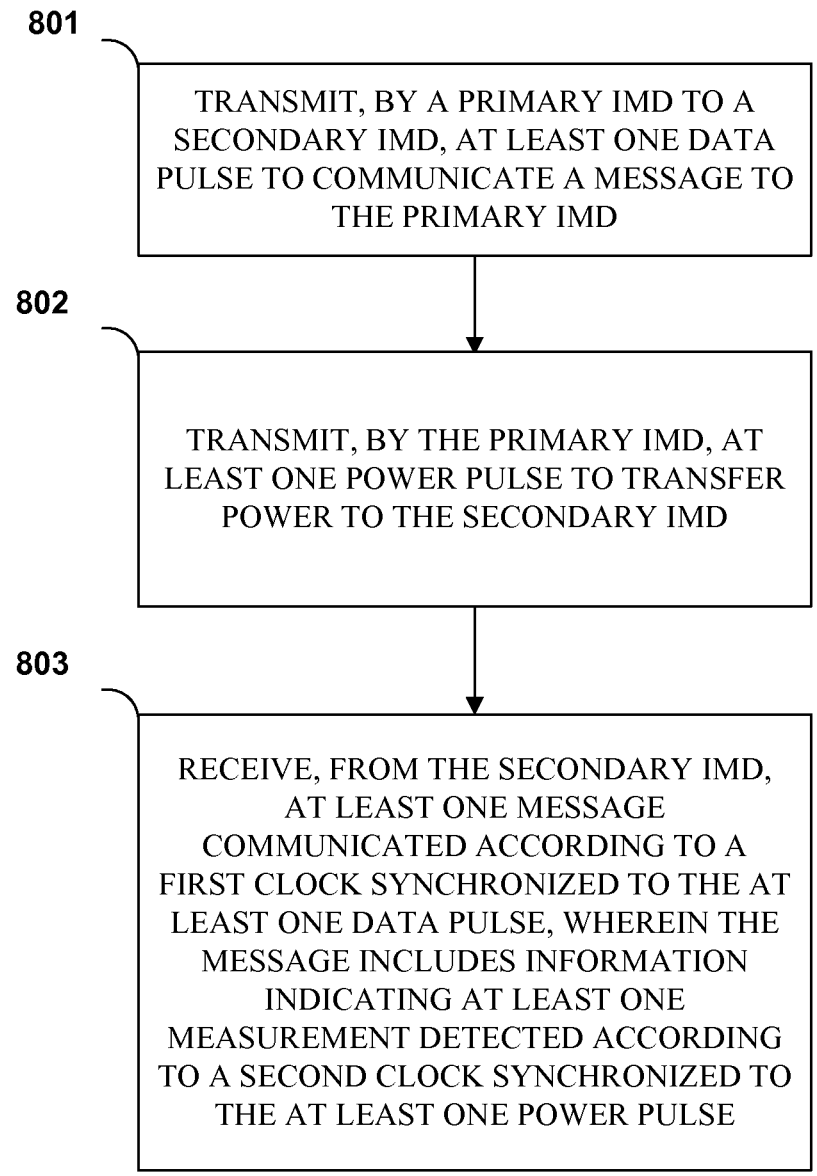
FIG. 8 is a flow chart diagram depicting one example of a method of operating a primary IMD consistent with this disclosure.

FIG. 8 is a flow chart diagram depicting one example of a method consistent with this disclosure. The method includes transmitting, by a primary implantable medical device (IMD) 10 at least one data pulse to communicate a message to a secondary IMD 20 (801). The method further includes transmitting, by the primary IMD 10, at least one power pulse to transfer power to the secondary IMD 20 (802). The method further includes receiving, from the secondary IMD 20, at least one message communicated according to a first clock 50 synchronized to the at least one data pulse, wherein the message includes information indicating at least one measurement detected according to a second clock 52 synchronized to the at least one power pulse (803).

Various methods for operating one or more primary and/or secondary medical devices are described herein. Any of the various methods described herein may be performed by a processor (e.g. primary IMD processor 30 and/or secondary IMD processor 40 as depicted in FIG. 2) under the control of computer-readable instructions. The computer-readable instruction may be stored in one or more computer-readable mediums, (memories) for execution by one or more processors to control either or both of the primary or secondary IMDs according to the methods described herein.

Various examples have been described. These and other examples are within the scope of the following claims.

The invention claimed is:

1. A system comprising:
    at least one primary implantable medical device (IMD) configured to operate based on a local clock;
    at least one secondary IMD communicatively coupled to the primary IMD and configured to receive at least one communication pulse and at least one power pulse from the primary IMD, wherein the at least one power pulse comprises a first power pulse and the secondary IMD is operable to estimate, based on the first power pulse, an estimated arrival time of a subsequent power pulse;
    wherein the secondary IMD comprises:
        a communications clock unit configured to generate a first clock of the secondary IMD based on the at least one communication pulse; and
        a general purpose clock unit configured to generate a second clock different than the first clock based on the at least one power pulse.

2. The system of claim 1, wherein the communications clock unit is configured to generate the second clock by synchronizing the second clock to the local clock of the primary IMD.

3. The system of claim 2, wherein the local clock of the primary IMD is based on a crystal oscillator.

4. The system of claim 1, wherein the first clock of the secondary IMD is an intermittent clock configured to turn off when the secondary IMD is not operating to communicate.

5. The system of claim 1, wherein the secondary IMD is further operable to detect, via at least one sensor of the secondary IMD, at least one condition based on an estimated arrival time of the subsequent power pulse.

6. The system of claim 1, wherein at least one sensor of the secondary IMD is operable to detect the at least one condition by turning off at least one detection operation during arrival of the subsequent power pulse based on the estimated arrival time.

7. The system of claim 1, wherein the communications clock unit is further operable to turn off the first clock when a communications pulse has not been detected for a predetermined amount of time.

8. The system of claim 1, wherein the communications clock unit is further operable to synchronize the first clock local to the sensor based on the at least one power pulse.

9. The system of claim 1, wherein the secondary IMD is configured to use the second clock to perform at least one operation of the secondary IMD, the at least one operation selected from the group consisting of:

define a time period for at least one sensor of the secondary IMD to detect one or more patient conditions;
identify a duration of a power-on reset signal for the secondary IMD;
access information stored in one or more memories of the secondary IMD; and
calibrate sensor elements of the secondary IMD.

10. A device, comprising:
means for receiving at least one communications pulse for communicating a message;
means for receiving at least one power pulse for powering the device, wherein the at least one power pulse comprises a first power pulse;
means for estimating, based on the second clock, an estimated arrival time of a subsequent power pulse;
means for generating a first clock based on the at least one communications pulse; and
means for generating a second clock different than the first clock based on the at least one power pulse.

11. The device of claim 10, wherein the first clock is a communications clock.

12. The device of claim 10, wherein the means for generating the first clock turn off the first clock when the device is not operating to communicate.

13. The device of claim 10, wherein the means for generating a second clock generate a general purpose clock.

14. The device of claim 10, further comprising means for detecting at least one condition based on the estimated arrival time of the subsequent power pulse.

15. The device of claim 14, further comprising: means for turning off at least one detection operation of at least one sensor during arrival of the subsequent power pulse based on the estimated arrival time.

16. The device of claim 10, wherein the device is configured to use the second clock to perform at least one operation of the device, the at least one operation selected from the group consisting of:

define a time period for at least one sensor of the device to detect one or more patient conditions;
identify a duration of a power-on reset signal for the device;
access information stored in one or more memories of the device; and
calibrate sensor elements of the device.

17. The device of claim 10, further comprising means for turning off the first clock when at least one data pulse has not been received for a predetermined amount of time.

18. The device of claim 10, wherein the means for generating the first clock also generate the first clock based on the at least one power pulse.

* * * * *